US006358236B1

(12) United States Patent
DeFoggi et al.

(10) Patent No.: US 6,358,236 B1
(45) Date of Patent: Mar. 19, 2002

(54) DEVICE FOR RECONSTITUTING MEDICAMENTS FOR INJECTION

(75) Inventors: John Mark DeFoggi, Waukegan; Arnold Bilstad, Deerfield; Ingrid McPhilliamy, Chicago, all of IL (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 09/129,898

(22) Filed: Aug. 6, 1998

(51) Int. Cl.[7] .......................... A61B 19/00; A61M 5/32

(52) U.S. Cl. ...................... 604/414; 604/403; 604/411; 604/416; 604/905

(58) Field of Search ................................ 604/129, 414, 604/187, 905, 403, 411, 415, 197, 200, 201, 272, 239, 205, 206, 406, 416; 220/200, 202, 203.01, 203.08, 203.13, 260, 265, 277–8, 89.1–89.2; 222/490, 540, 541.1–541.3, 566–67

(56) References Cited

U.S. PATENT DOCUMENTS

| | | | | | |
|---|---|---|---|---|---|
| 1,705,763 | A | * | 3/1929 | Hasbrouck | |
| 2,748,769 | A | * | 6/1956 | Huber | 128/221 |
| 3,776,239 | A | * | 12/1973 | Cooley | 128/347 |
| 4,058,121 | A | * | 11/1977 | Choksi et al. | 128/221 |
| 4,340,068 | A | * | 7/1982 | Kaufman | 128/766 |
| 4,543,101 | A | * | 9/1985 | Crouch | 604/411 |
| 4,588,403 | A | * | 5/1986 | Weiss et al. | 604/411 |
| 4,662,878 | A | | 5/1987 | Lindmayer | |
| 4,826,492 | A | * | 5/1989 | Magasi | 604/274 |
| 4,838,877 | A | * | 6/1989 | Massau | 604/272 |
| 5,254,106 | A | * | 10/1993 | Feaster | 604/272 |
| 5,507,730 | A | * | 4/1996 | Habar et al. | 604/187 |
| 5,569,209 | A | * | 10/1996 | Roitman | 604/190 |
| 5,653,698 | A | * | 8/1997 | Niedospial et al. | 604/283 |
| 5,772,652 | A | * | 6/1998 | Zielinski | 604/411 |
| 5,887,755 | A | * | 3/1999 | Hood, III | 222/135 |
| 6,019,750 | A | * | 2/2000 | Fowles et al. | 604/403 |
| 6,070,623 | A | * | 6/2000 | Aneas | 141/329 |

FOREIGN PATENT DOCUMENTS

| | | |
|---|---|---|
| EP | 0 587 347 A1 | 3/1994 |
| FR | 2 753 624 | 9/1996 |

* cited by examiner

*Primary Examiner*—Angela D. Sykes
*Assistant Examiner*—Patricia Bianco
(74) *Attorney, Agent, or Firm*—Larson & Taylor PLC

(57) ABSTRACT

A device is provided for reconstituting a lyophilized or powdered medicament such as blood factor VIII which must be reconstituted just prior to use, such as by introduction of a sterile fluid from a syringe, which comprises a housing having an upper section capable of receiving a syringe and a lower section capable of receiving a vial containing the medicament in co-axial alignment with the syringe, a middle section connecting the upper and lower sections which has a central aperture which forms a passageway for fluid transfer between the syringe and the vial, and a hollow vented spike which extends downwardly from the central aperture for a length sufficient to ensure that the lower end of the spike will pierce the seal and enter the interior of a vial housed in the lower section of the device. The invention is advantageous because the vented opening in the spike will allow for an equalization of the pressure after the piercing of the vial by the spike which will facilitate the use of the device. In addition, the device also features an ergonomic design which maximizes the safety and efficiency of the reconstitution of important medicaments such as blood factors, and allows for easily manipulation of the device by patients such as those with Factor VIII deficiency who may suffer from related physical ailments which limit their dexterity.

33 Claims, 8 Drawing Sheets

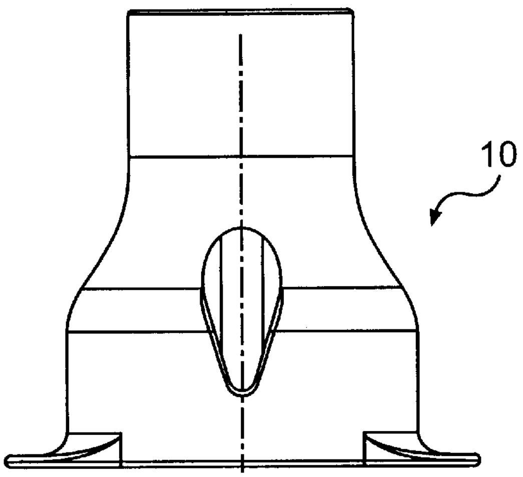
FIG. 2D
FIG. 2E
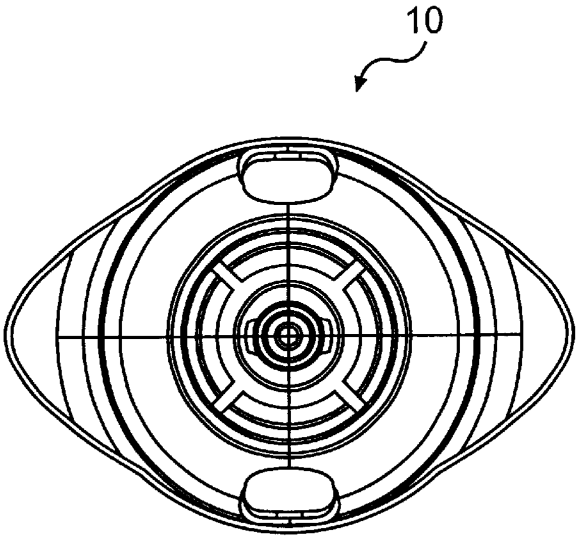
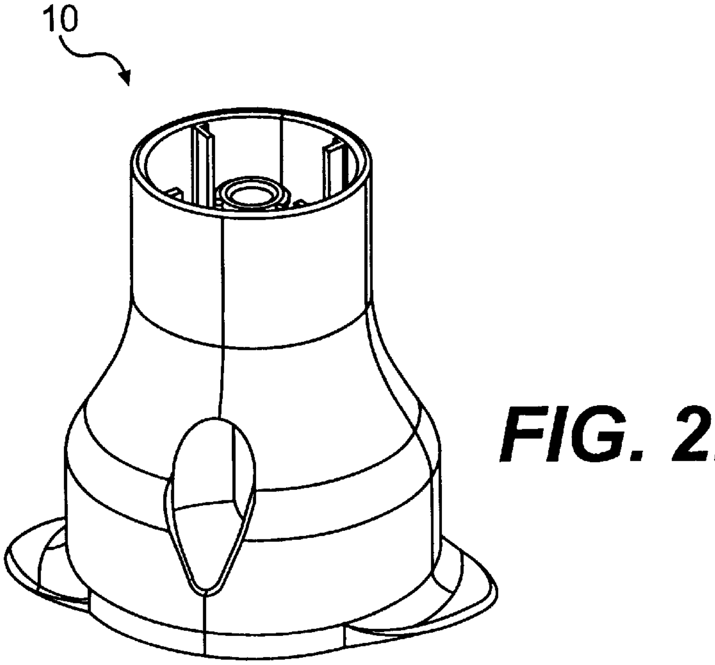
FIG. 2F

DEVICE FOR RECONSTITUTING MEDICAMENTS FOR INJECTION

FIELD OF THE INVENTION

This invention relates in general to a device for use in reconstituting medicaments into a solution suitable for injection into a patient, and in particular to a safe and ergonomic reconstitution device suitable for use with a syringe containing a fluid such as sterile water and a vial containing a lyophilized or powdered product, such as factor VIII, which provides a fluid passageway between the syringe and the vial, and includes a central vented spike extending from the middle of the device piercing the vial, and which has an overall design which greatly facilitates reconstitution of important blood factors.

BACKGROUND OF THE INVENTION

Over the past few years, many patients suffering from blood diseases such as hemophilia who require daily intravenous injections have benefitted from the increased availability of lyophilized (freeze-dried) concentrates of blood factors such as Factor VIII. These freeze-dried blood factor concentrates, such as RECOMBINATE® brand recombinant factor VIII protein manufactured by Baxter Healthcare Corporation, are extremely advantageous in that they may be readily stored for longer periods of time prior to use with less risk of contamination. As a result, these products are ideal for home use and have benefitted many patients who can utilize these products on their own and avoid costly and time-consuming in-patient procedures at a clinic or hospital in order to receive the necessary injections.

However, a major drawback to the widespread use of blood factor concentrates on an out-patient basis has been the need to efficiently and safely reconstitute the lyophilized product prior to injection into the patient. In particular, there are several obstacles that must be overcome by patients who would like to use these lyophilized concentrates at home. First and foremost, most conventional methods of reconstitution currently require the use of a hypodermic syringe that pierces the stopper of a vial containing the lyophilized product, and thus the dangers associated with exposed hypodermic needles at any point of the process must be reduced or eliminated. Considering that the major users of these concentrates will be hemophilia patients, one can easily recognize the great potential harm if such a person is inadvertently pricked by a hypodermic needle.

Moreover, another major obstacle that must be overcome is that the primary users of blood factor concentrates will be patients with hemophilia (Factor VIII deficiency) who often suffer from joint damage and as a result face substantial physical obstacles in manipulating the devices which must be used in order to reconstitute the dried product and inject the resulting solution. As a result, it is important that a means be developed which will allow such patients to reconstitute and utilize a concentrated blood product without requiring undue pressure or force, and without the need for complex manipulation that may be difficult or impossible for a hemophilia patient to carry out.

Finally, keeping in mind that the average patient will not be a trained healthcare professional, it is extremely important that a device for use in reconstituting a dry blood factor concentrate be intelligently and ergonomically designed so that the patient will easily understand how to operate it safely and effectively. For example, since the reconstitution process will very often make use of a glass syringe or vial, it is necessary that the patient be able to grasp such a device properly so as to avoid any possibility of breaking the syringe or vial which, for reasons as stated above, will increase the chance of an inadvertent cut which would be of great potential harm. In addition, since the blood factor concentrates themselves are often expensive, it is very important for the patient to be able to maximize the reconstitution of the lyophilized concentrate in the vial, and to minimize any steps where inadvertent loss or spillage of this concentrate might occur.

At present, although there have been many devices that have been developed which relate to the reconstitution of a medicament using a syringe which injects a fluid into a vial, no one prior reconstitution device or system has been able to overcome all of the above-mentioned obstacles and provide an ergonomic, safe and effective means for reconstituting a blood factor concentrate which can be utilized by the patient at home if necessary without assistance from a healthcare professional. Among the many devices in this field include those disclosed in U.S. Pat. Nos. 5,554,128; 5,520,659; 5,247,972; 5,158,558; 5,171,214; 5,137,511; 5,125,908; 5,088,996; 4,834,149; and 4,768,568.

However, in no cases do these references provide a simple, safe and effective reconstitution system or device which is ergonomically designed to maximize ease of use by a patient, and which can be safely and efficiently operated so as to maximize the reconstitution of a blood factor concentrate, while minimizing or avoiding problems associated with breakage of the syringe or vial, inadvertent exposure of the syringe needle, and inadvertent loss or spillage of the valuable and expensive blood factor concentrate that will be injected into the patient.

SUMMARY OF THE INVENTION

Accordingly, it is thus an object of the present invention to provide a reconstitution device which can be used safely and effectively by hemophilia patients which eliminates the possibility of the user being inadvertently pricked by an exposed hypodermic needle during the reconstitution process.

It is further an object of the present invention to provide an ergonomically designed reconstitution device which can facilitate the reconstitution of a lyophilized product such as a blood factor concentrate so that it can readily be operated by a human patient on an out-patient basis without the need for assistance by a healthcare professional.

It is even further an object to provide a safe and effective reconstitution device which contains means to equalize pressure during the piercing of a stopper on a sterile, vacuum-packed vial.

It is still further an object of the present invention to provide a reconstitution device which is easy to manipulate, and which does not require excessive force or pressure to be operated so that it can be readily used even by elderly patients or patients suffering from joint disease or other physical limitations.

These and other objects are achieved by virtue of the present invention which provides a reconstitution device for use in reconstituting a lyophilized product contained in a sealed vial using fluid introduced into the vial by means of a syringe, said reconstitution device comprising a housing having an upper section capable of receiving a syringe and a lower section capable of receiving a vial, said upper and lower sections positioned so that the syringe and vial are in co-axial alignment, and a middle section connecting the upper and lower sections having an aperture through which fluid from a syringe housed in the upper section can be introduced into a vial housed in the lower section, and having a central vented spike extending downwardly from the aperture in the middle section which extends to a length sufficient to ensure that the lower end of the spike will enter the interior of a vial when housed in the lower section. The vented opening in the central spike is advantageous primarily because it will allow for an equalization of the pressure following the piercing of the stoppered vial by the sharpened end of the spike. In the preferred embodiment, the outermost portion of the lower section will be flared and will contain flanges so as to provide a suitable shape for proper gripping and manipulation of the reconstitution device which will facilitate proper use of the device and virtually eliminate mishandling of the syringe or vial which could result in inadvertent breakage and potential injury to the patient.

These and other objects and advantages of the invention will be disclosed in, or become apparent from, the detailed description of the preferred embodiments provided hereinbelow.

BRIEF DESCRIPTION OF THE DRAWINGS

The present invention will now be described in detail with respect to preferred embodiments thereof, which are to be taken together with the accompanying drawings, wherein:

FIG. 2D is a front view of the reconstitution device as shown in FIG. 1.

FIG. 2E is a top view of the reconstitution device as shown in FIG. 1.

FIG. 2F is a top perspective view of the exterior of a reconstitution device in accordance with the invention.

DETAILED DESCRIPTION OF THE PREFERRED EMBODIMENTS

Figure 4A:
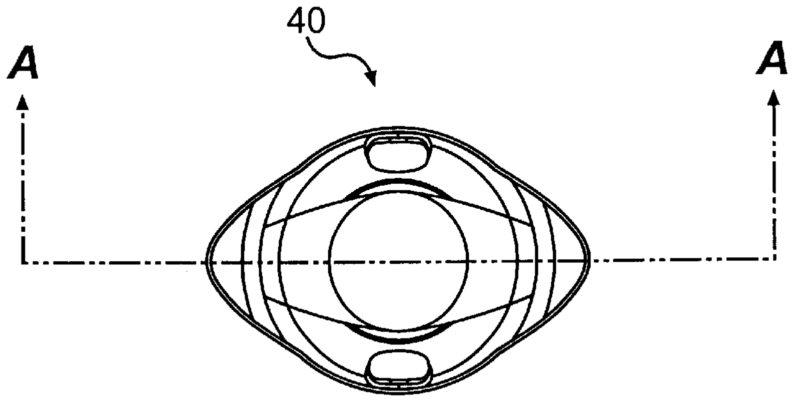
FIG. 4A is a top view of the combination reconstitution device and syringe as shown in FIG. 3.

In accordance with the present invention, a reconstitution device is provided which allows for safe and efficient reconstitution of a lyophilized medicament, such as a blood factor concentrate, in a vial or other suitable container, which is reconstituted into solution by means of a sterile fluid transmitted into the vial by a syringe, after which the reconstituted solution is withdrawn back into the syringe prior to its injection into a patient. In the preferred embodiment, such as that best shown in FIGS. 1 and 2A–G, the reconstitution device 10 of the present invention comprises a housing 12 containing an upper section 14 designed to receive and house a syringe, and a lower section 18 designed to receive and house a stoppered or sealed vial which contains a lyophilized or powdered medicament that must be reconstituted prior to use. In a particularly preferred embodiment, the upper section 14 is roughly cylindrical and will have an exterior opening 15 and interior surface 11 which are of a size and shape suitable to receive a syringe 16, as best observed in FIGS. 3 and 4A–4B. When properly mated with the device 10 of the present invention, the syringe 16 will be centrally positioned in the interior of upper section 14 so that the opening 47 at the proximal end 13 of the syringe (i.e., the end closest to the attachment point of the syringe to the device 10) will be aligned with the central aperture 21 of the middle section 22 which connects the upper and lower sections. If so desired, one or more ribs 24 may be positioned on the interior surface 11 of the upper section 14 to provide additional stability to the syringe when housed in the upper section, and these ribs may be employed so as to allow syringes of different sizes to be utilized with the reconstitution device of the present invention.

Figure 1:
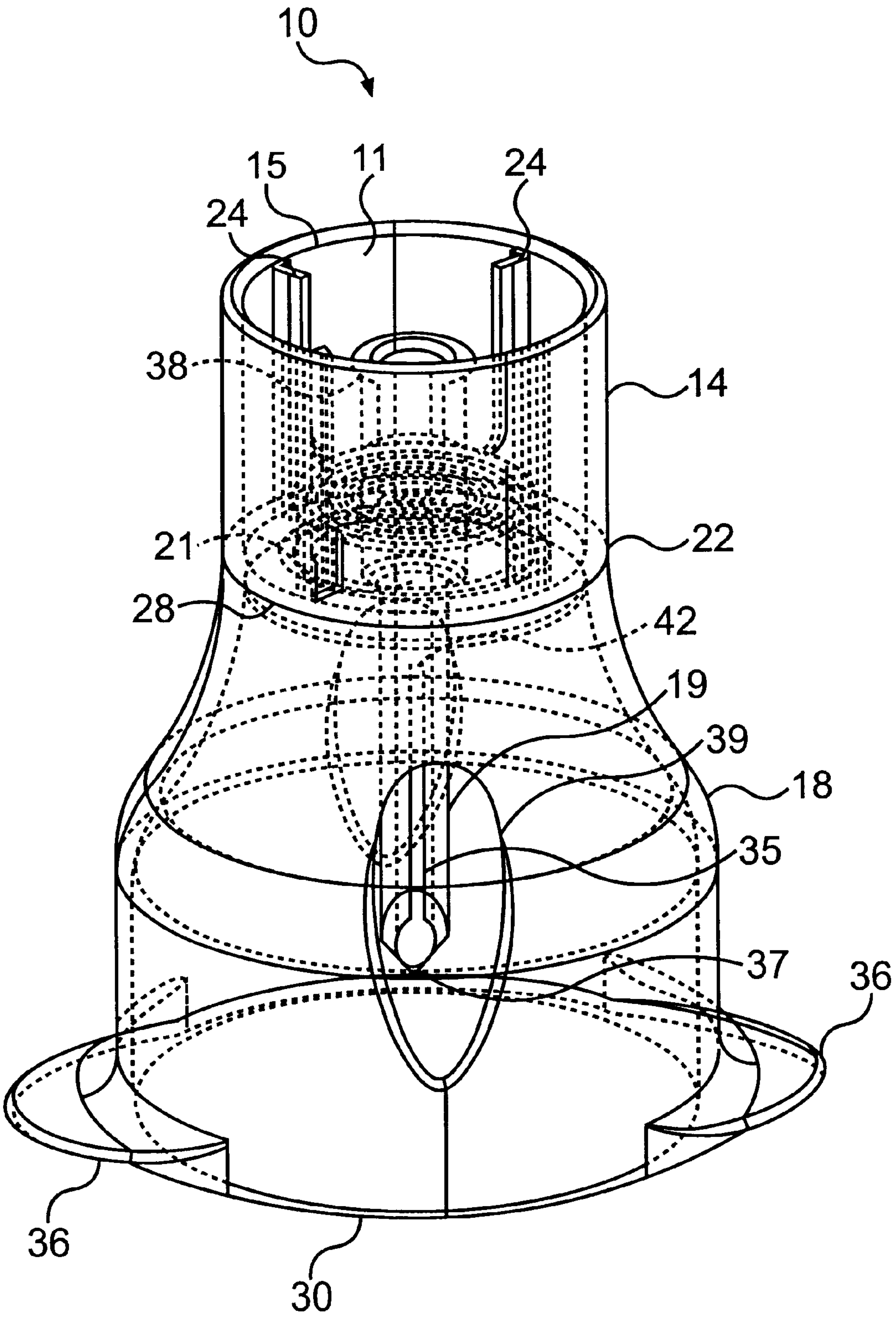
FIG. 1 is a perspective view of a preferred embodiment of a reconstitution device in accordance with the present invention which also depicts the interior features of the device.
Figure 2A:
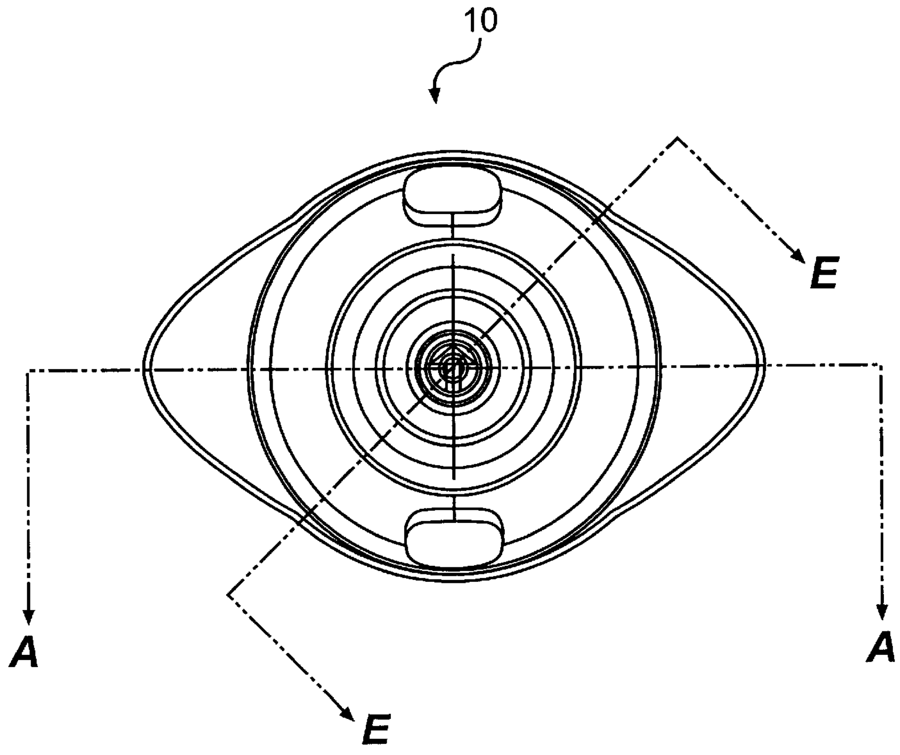
FIG. 2A is a bottom view of the reconstitution device as shown in FIG. 1.
Figure 2B:
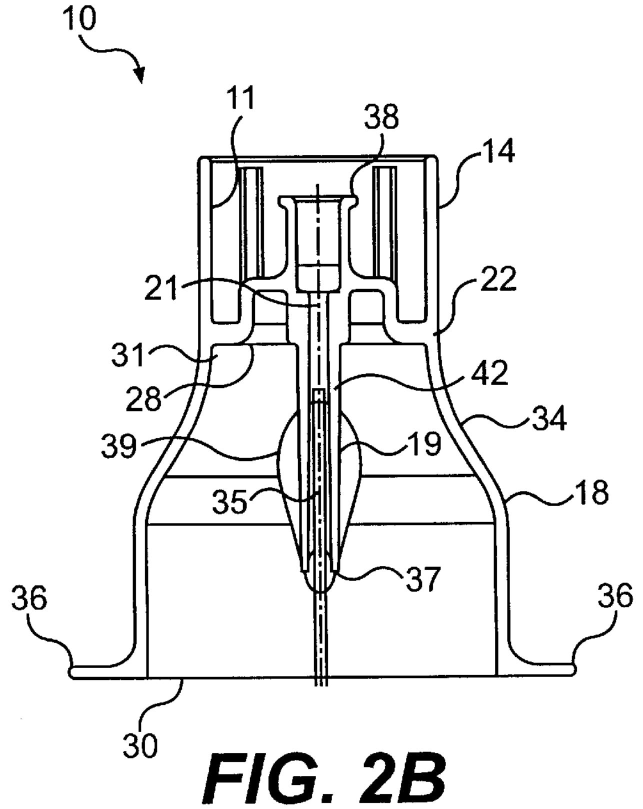
FIG. 2B is a cross-sectional view of the reconstitution device as shown in FIG. 2A taken along the line A—A.
Figure 2C:
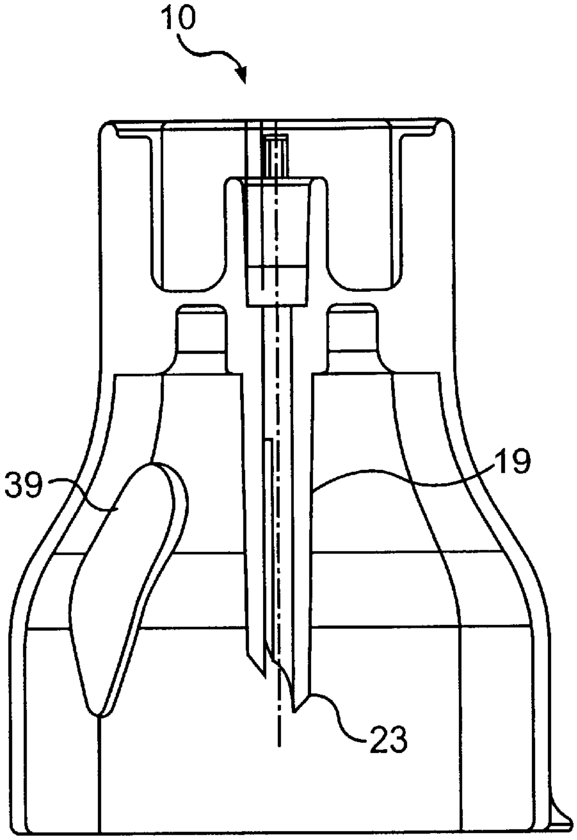
FIG. 2C is a cross-sectional view of the reconstitution device as shown in FIG. 2A taken along the line E—E.
Figure 2G:
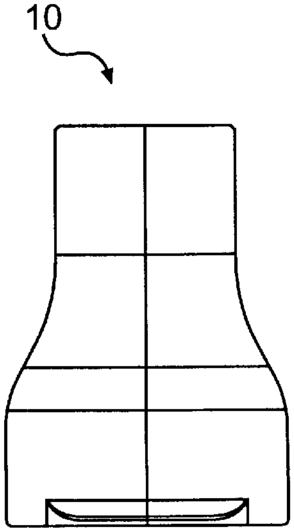
FIG. 2G is a side view of the reconstitution device as shown in FIG. 1.
Figure 3:
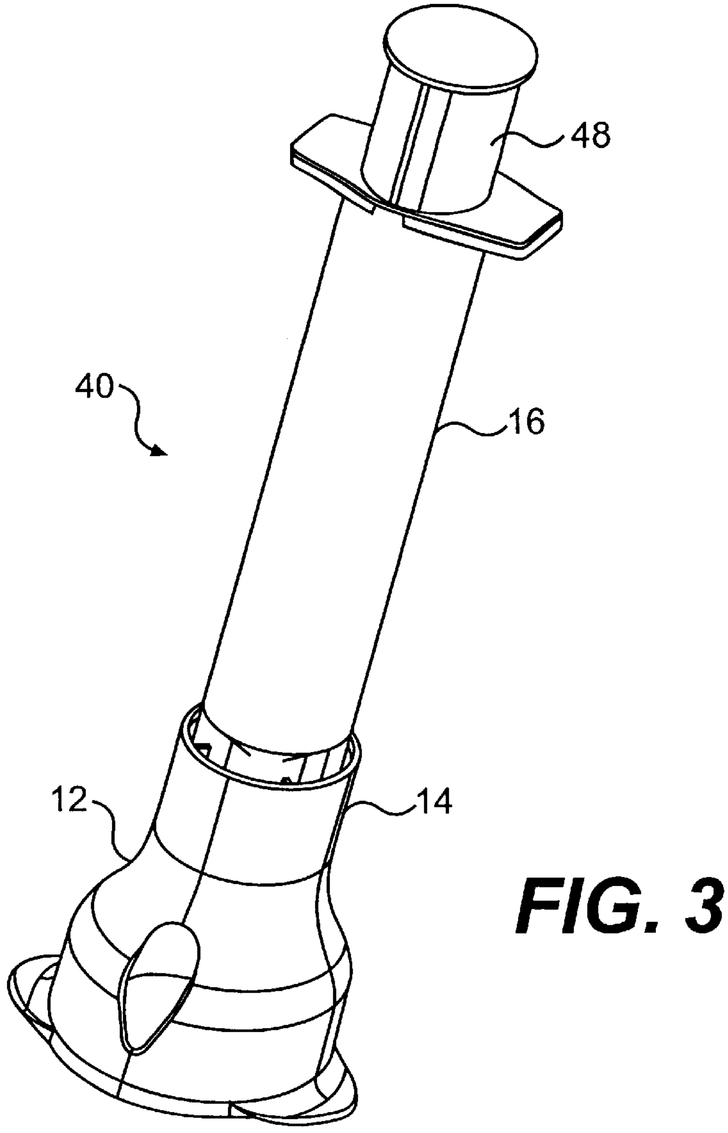
FIG. 3 is a perspective view of a reconstitution device of the present invention in combination with a syringe.

In the preferred embodiment, the lower section 18 of the device 10 will extend downwardly from the upper section 14 and will be configured so as to house a vial 20, such as is shown in FIGS. 5 and 6A–6D, which contains a sealed powdered or lyophilized medicament. As such, it is preferred that the inner end 28 of lower section 18 have a roughly cylindrical interior surface which is designed to house the top end 32 of the sealed vial 20. However, in the particularly preferred embodiment, the outer end 30 of the lower section 18 will be flared so that the exterior opening of the lower section will have a diameter greater than that of the inner end 28 of the lower section 18. As shown in particular in the drawing FIGS. 1 and 2A–2G, in the preferred embodiment, the exterior surface of the lower section 18 of housing 12 is tapered or flared gradually in the outward direction to create a "neck" 34 which will provide a location which the user can grip or push against. Preferably, as shown in FIG. 1 and 2B, the neck provides a smooth surface without sharp edges. This is advantageous for hemophilia patients in order to minimize the risk of cuts and bruises when using the device, and also to make the device easier to use for those with joint damage.

Similar assistance in gripping and manipulating the reconstitution device of the invention can be provided in the form of gripping flanges 36 which are preferably disposed on the exterior of the opening at the outer end 30 of the lower section 18, and are sized so that they may be gripped by fingers when pushing the device onto a vial or when withdrawing fluid from the vial with a syringe. These added features of the invention provide for an ergonomically designed reconstitution device which will not only be self-instructive to the user, but which will facilitate overall operation of the device. These gripping features will also provide an important advantage to hemophilia patients, many of whom suffer from varying degrees of joint disease, and who may otherwise require assistance in manipulating and using other syringe/vial systems that have been used in the reconstitution of a medicament.

In the preferred embodiment, the reconstitution device 10 will be constructed so that the interior surface 31 of the inner end 28 of lower section 18 will be adapted to receive and house the upper end 32 of a sealed vial 20, and although a variety of shapes and sizes of this feature are possible, inner end 28 will preferably be designed to receive a conventional vial having a volume in the range of about 10 to 50 ml, such as a 30 cc vial. As such, the inner end 28 of lower section 18 will preferably be roughly cylindrical in configuration.

It is also preferred that the outer end 30 of the lower section 18 of the device will only extend lengthwise so far as to cover a portion of the vial 20 and not the entire vial. The reason that the reconstitution device preferably does not extend all the way to the bottom of the vial is that in the desired manner of operation, as will be set forth in more detail below, the user first attaches the combined syringe and reconstitution device 40 over the sealed end of the vial so that the spike 19 pierces the vial and establishes a complete fluid pathway from the syringe to the vial. However, at this point, the user will generally want to grasp the lower end of the vial so as to gently shake or swirl the vial and ensure complete reconstitution of the solid material therein. In addition, since the sealed vial is normally kept refrigerated, it is often desired by the user that the material in the vial be warmed by hand during the reconstitution process so that the resulting reconstituted solution approaches body temperature before being injected into the patient.

Finally, as will be set forth below, in the preferred manner of operation, following the introduction of the fluid from the syringe into the vial and the reconstitution of the medicament therein, the entire combination of vial, reconstitution device and syringe will be inverted by the patient so that the vial is situated at the top of the device and syringe, which will assist in allowing the reconstituted solution to be introduced back into the syringe. The fact that the lower section of the present device is of a length which allows the user to grasp the bottom of the vial while the device itself is still in place on top of the vial will thus facilitate all of the above operations. Preferably, the lower section of the device will extend from approximately one-third to about two-thirds the length of the vial, and it is particularly preferred that the lower section extend to about half the length of the vial. A combination 50 of the recombination device 10 of the present invention and a conventional sealed vial 20 is shown in FIGS. 5 and 6A–6D.

The device 10 of the present invention also preferably includes a middle section 22 which connects the upper and lower sections and which has a central aperture 21 which forms a passageway for the transfer of fluid between the syringe and vial. In the preferred embodiment, the middle section will also be provided with means, such as luer fitting 38, by which the syringe can be maintained in proper position during the reconstitution process. In the preferred embodiment, the opening 47 at the proximal end 13 of the syringe 16 can be mated with the luer fitting 38 or other suitable means provided on the middle section 22 which will attach to reciprocal means on the syringe. By achieving a proper mating, these attachment means will be used to ensure that the fluid being expelled by the syringe will only be directed through the middle section of the device 10, and will eventually enter the vial 20 so as to reconstitute the lyophilized or powdered medicament therein, as will be described more fully below. It is preferred that the mating between the syringe 16 and the upper section 14 of the reconstitution device be one that is readily engaged and readily disengaged when so desired by the user, and thus any suitable means to accomplish this objective can be used, such as a luer fitting 38 or other mating means as described above which allow for the syringe to be screwed into the upper section of the device and subsequently unscrewed without much difficulty, as would be understood by one skilled in this art.

In the particularly preferred embodiment, the device 10 further comprises a hollow vented spike 19 which extends downwardly from the central aperture 21 for a length sufficient to ensure that the lower end of the spike will pierce the seal 43 at the top of the vial when the vial is received and housed at the inner end 28 of the lower section 18 of the device. As can be best observed in FIGS. 1 and 2C, the spike 19 has an angled profile at its lowermost end 23 which allows it to pierce the seal or stopper 43 of a vial 20 when the device 10 is positioned on top of the vial, and is hollowed at its center so as to provide a continuation of the passageway through the middle section 22 which will allow fluid from the syringe to be introduced into the vial.

Figure 6A:
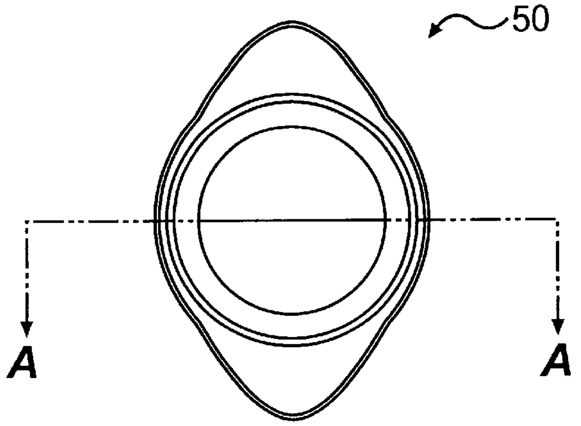
FIG. 6A is a bottom view of the combination reconstitution device and vial as shown in FIG. 5.
Figure 6B:
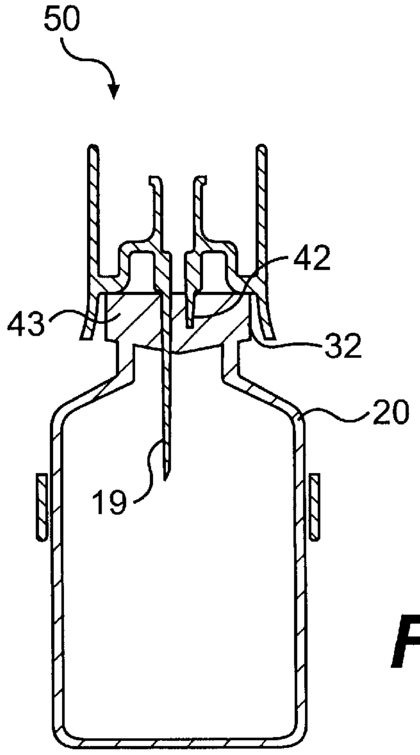
FIG. 6B is a cross-sectional view of the combination reconstitution device and vial as shown in FIG. 6A taken along the line A—A.
Figure 6C:
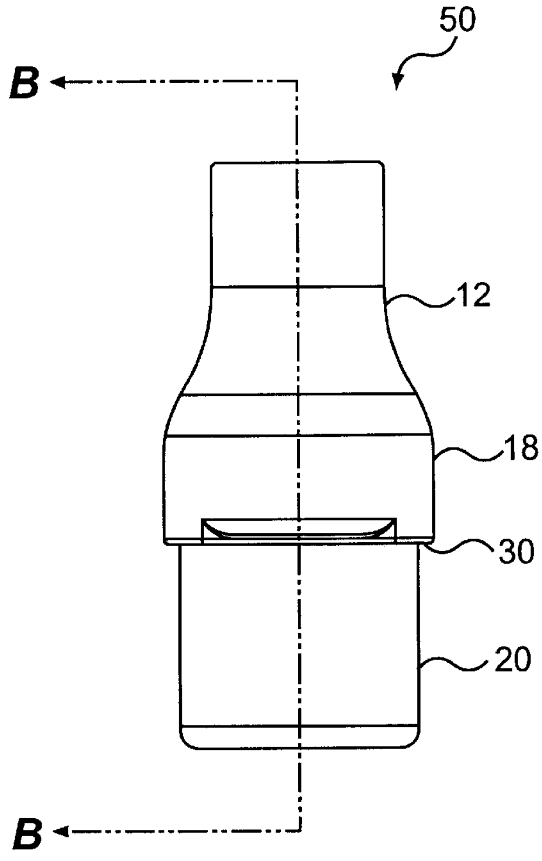
FIG. 6C is a side view of the combination reconstitution device and vial as shown in FIG. 5.
Figure 6D:
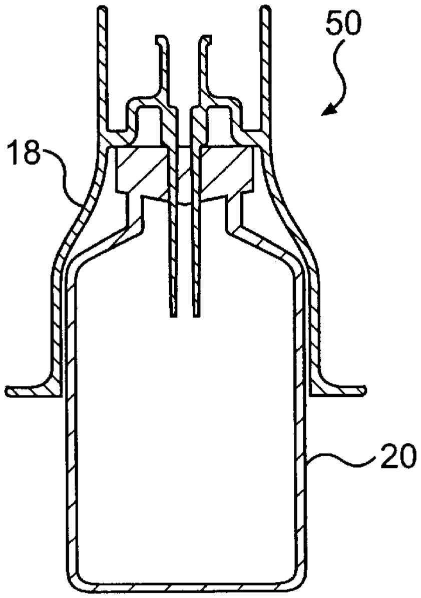
FIG. 6D is a cross-sectional view of the combination reconstitution device and vial as shown in FIG. 6C taken along the line B—B.

In addition, the spike 19 has a elongated slot or vent 35 along its side which extends from the lower end 37 of the spike 19 to a point 42 located at the base of the spike just below the middle section 22 of the device 10, as best observed in FIGS. 1 and 6B. This hollow vented spike 19 is provided primarily as a means of equalizing pressure as the spike pierces the seal of the vial which normally will be vacuum-packed. This feature thus allows for rapid equalization of pressure in the vial which ideally will attain atmospheric pressure within a second or two of being pierced by the vial. By releasing the vacuum from the vial, fluid from the syringe can be introduced into the vial with less force, at a lower velocity, since the fluid is not being pulled into the vial by the vacuum. This minimizes foaming of the reconstituted product. The positive pressure which builds up in the vial through the introduction of the fluid also has the beneficial effect of making it easier to withdraw the reconstituted product into the syringe with a minimum of effort. In the preferred embodiment, this spike 19 may be provided with a tip protector (not shown) to protect the spike and maintain sterility until such time that the user begins the reconstitution process.

Another advantage obtained by the slotted opening in the spike is that in the preferred manner of operation, as will be described further below, following the introduction of the fluid from the syringe into the vial and the reconstitution of the solid medicament contained in the vial, the entire apparatus, including vial, reconstitution device and syringe, is turned upside down so that the reconstituted medicament will flow back through the central aperture of the reconstitution device and into the syringe where it can then be injected into the patient by any suitable means. By providing a slotted opening or vent in accordance with the present invention, when the device is inverted so as to dispense the reconstituted medicament from the vial into the syringe, drainage of all the liquid from the vial, even that which is found at the lowest level in the vial, will be possible. This is extremely beneficial to the user who will be able to make complete use of the blood product in the vial, particularly in light of the fact that medicaments such as lyophilized blood factors are usually quite expensive, and also in light of the fact that a full dosage of the blood factors are often required to be totally effective.

In another preferred embodiment (not shown), the spike may be configured such that the outer diameter of the spike is smaller at the tip than at the base of the spike. In such an embodiment, a portion of the spike at its tip may be one diameter, after which the spike widens to a second diameter for the remainder of its length. By employing this embodiment, a user of the present device would sense an intermediate point at the juncture of the narrower length of spike and the wider portion. Such an intermediate point can be used as a signal to wait until the vacuum pressure is completely released through the slotted opening before a user continues inserting the spike into the vial.

In another preferred embodiment of the invention, a filter (not shown) for particulate matter can be incorporated in the device 10 at any suitable point along the fluid pathway between the vial and the syringe. The filter is advantageous in that it can prevent undesirable larger particles from entering the syringe which could otherwise cause a blockage in the syringe and prevent it from operating properly. In addition, such a filter can also control the maximum size of the particulates that will ultimately be injected back into the patient after reconstitution of the medicament. In the preferred embodiment, this filter is a conventional mesh filter comprised of a suitable material such as nylon or polyester and most preferably has a pore size of from about 80 to about 160 microns. In addition, it is particularly preferred that the filter be disposed in the central aperture 21 of the middle section 22 of the device 10, and this can be done, for example, by taking a section or ribbon of a suitable filter material, punching out an appropriately sized piece, and welding the filter at a suitable point in the central aperture of the middle section, such as in the center of the luer fitting, using conventional methods such as sonic welding.

In the preferred embodiment, the reconstitution device of the present invention, including upper, lower and middle sections and the hollow vented spike 19, is comprised of any suitable rigid plastic material that can withstand normal sterilization procedures. Particularly preferred materials include any suitable polycarbonate plastic, however, a variety of other plastic materials, such as acrylics or acrylic butyl styrene (ABS), will also be suitable, as would be recognized by one skilled in this art. Accordingly, the device can be constructed out of a transparent or opaque material if so desired.

In another preferred embodiment of the invention, the device further comprises openings, such as the tear-drop shaped openings 39 in the lower section of the device, by which a visual assessment can be made with regard to the introduction of the spike 19 into the vial 20 so as to ensure proper positioning of the spike and proper transmission of the fluid from the syringe into the vial. The openings 39 may be a variety of shapes, but are preferably elongated along the axis of the spike in order that a user may visualize the spike and the fluid in the vial. The openings 39 are also preferably of a size small enough to prevent the insertion of a finger therethrough.

Figure 4B:
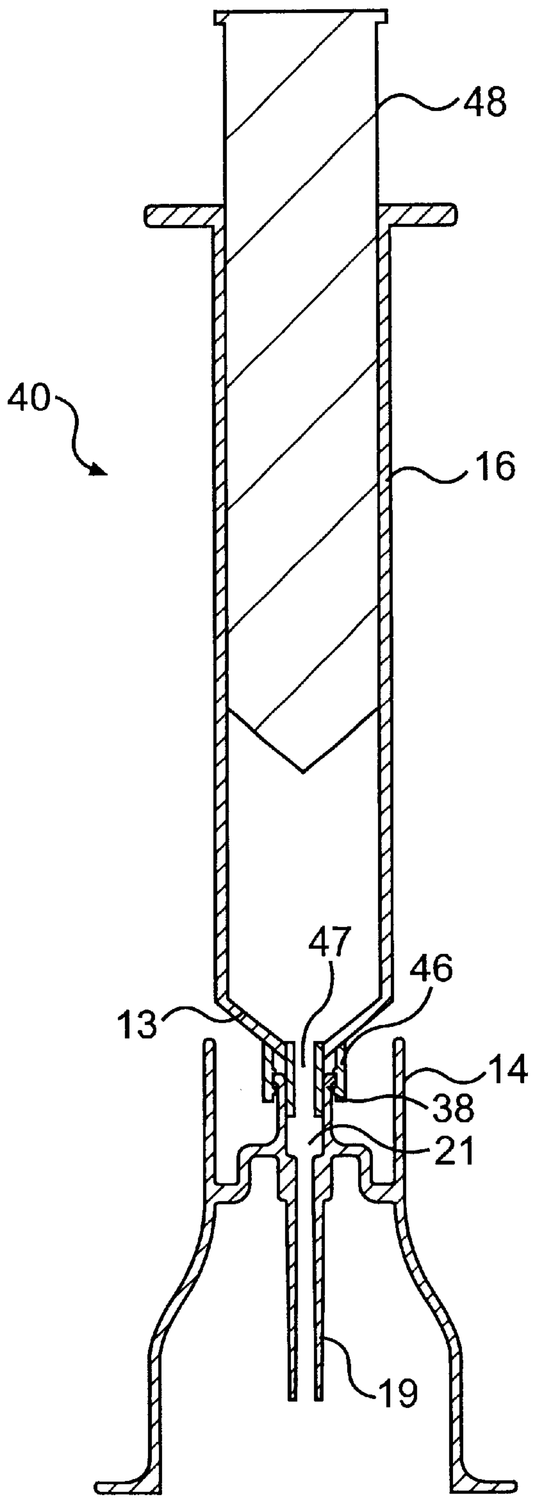
FIG. 4B is a cross-sectional view of the combination reconstitution device and syringe as shown in FIG. 4A taken along the line A—A.
Figure 5:
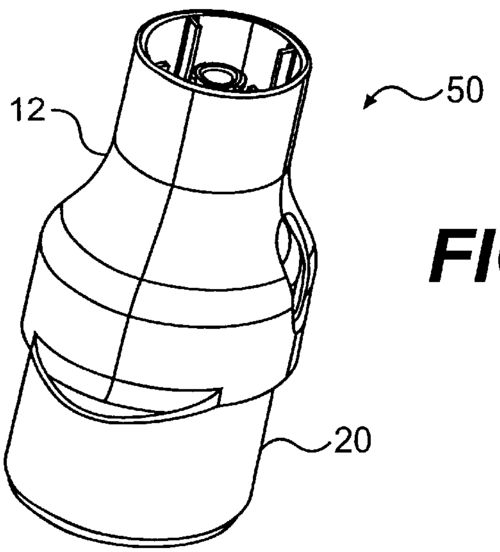
FIG. 5 is a perspective view of a reconstitution device of the present invention in combination with a vial.

In addition, as one skilled in the art would understand, the reconstitution device of the present invention can be used with a variety of suitable syringes that are currently available, including those conventional syringes produced by companies such as Becton Dickinson, Terumo, and Schott Parenta. In the preferred embodiment, the syringe used with the reconstitution device of the invention comprises a syringe 16 of the general type shown in FIGS. 3 and 4A–4B which can retain a sterile fluid such as sterile water for injection, or any other suitable fluid such as saline, half-normal saline or dextrose, that would be used for reconstitution depending on the nature of the material to be reconstituted. At the proximal end of the syringe, i.e., the end at which the syringe is attached to the reconstitution device, the syringe will include an attachment means, such as luer fitting 46, which will mate with an appropriate reciprocal attaching means disposed on the middle section 22 of the housing 12. The attaching means 46 on the syringe 16 is preferably one that will allow the syringe to be readily screwed into position in the upper section 14 of the reconstitution device and then to be readily unscrewed following completion of the reconstitution process, but as would be understood by one skilled in the art, numerous other means of attachment to achieve this purpose will be possible. As best shown in FIG. 4B, the luer fitting 46 will have a central opening 47 that will allow fluid from the syringe to be transmitted through the central aperture 21 and hollow spike 19 of the reconstitution device 10 and into a vial 20 housed in the lower section of the device.

In the preferred embodiment, the reconstitution device of the invention is employed in combination with a syringe attached thereto, and this device/syringe combination 40 is preferably lowered onto vial 20 so that the hollow spike 19 of the device 10 pierces the sealed opening of the vial 20, and the fluid from the syringe 16 can be introduced into the vial so as to reconstitute the powdered or lyophilized medicament contained therein. In operation, a plunger 48 or other similar device may be employed which will assist in expelling the fluid from the syringe through the reconstitution device and into the vial containing the medicament to be reconstituted. After the medicament has been reconstituted, the plunger or other suitable tool may be pulled in the opposite direction so as to withdraw the reconstituted fluid from the vial back into the syringe. As indicated below, the preferred method of carrying out this operation is to maintain the syringe, device and vial in upright position at the time that reconstitution of the medicament occurs, and then invert this combination so that the inverted vial is situated above the reconstitution device and syringe, and drainage of the fluid in the vial will occur.

As has been described with regard to the above elements of the reconstitution device of the invention, and the syringe and vial used therewith, the preferred manner of operation of the device is to provide a syringe that has been filled with a suitable sterile fluid such as sterile water for injection, and attach the syringe to the reconstitution device prior to the placement of the reconstitution device over the sealed vial. In the preferred embodiment, the reconstitution device with attached syringe can be made available to the user as a combination which can be sold either with or without the vial containing the medicament that needs to be reconstituted. Accordingly, the syringe/device combination can be sterilized and/or sealed together in suitable sterile packaging prior to use. In addition, as set forth above, a tip protector may be provided which will be disposed over the hollow spike of the lower section of the reconstitution device so as to further ensure the sterility of the spike prior to use. Even further, a means can be provided by which the potential user could visually assess if the syringe or the reconstitution device was opened and made unsterile prior to use. Such a means would comprise any of the many conventional tamper-evident packaging means presently employed for a variety of applications regarding medical or consumer products. For example, tamper-evident packaging could be provided around the attachment of the syringe to the reconstitution device which will break should the syringe be unscrewed from the device prior to use.

In any event, in the preferred manner of operation, the user will take the combination of the syringe and reconstitution device, after removing the tip protector if present, and place the combined device over a sealed vial which contains a medicament, such as a lyophilized factor VIII concentrate, e.g., RECOMBINATE® produced by Baxter Healthcare Corporation, so that the vial is received in the interior of the lower section of the device housing 12. In some cases, the stoppered vial containing the factor VIII concentrate or other valuable medicament will further contain a sterile cover protector or "pop-top" made of plastic or other moldable material which may be provided to further ensure the cleanliness and sterility of the vial, and this "pop-top" cover must be removed prior to the reconstitution process.

As stated above, when the vial and spike have been made ready for reconstitution, the vial is placed under the reconstitution device so that its hollow vented spike may pierce the seal or stopper at the upper end of the vial and create a fluid pathway from the syringe to the vial. In the preferred method, sterile fluid from the syringe is expelled via a plunger or other suitable means so that it travels through the central aperture and spike in the middle section of the reconstitution device and enters into the vial containing the medicament to be reconstituted. At the point where the sterile fluid from the syringe has been fully introduced into the vial, the user will preferably gently shake or swirl the vial to promote maximum reconstitution of the solid medicament in the vial.

Following the reconstitution step, the entire combination of syringe, reconstitution device and vial is preferably inverted so that the vial is positioned above the reconstitution device and the syringe. At this point, the reconstituted fluid will drain into the syringe, and this drainage can be aided by means of pulling a plunger or other suitable device which will draw fluid from the vial back into the syringe. Preferably, as stated above, the reconstituted fluid will have passed through a suitable filter disposed in the reconstitution device at a suitable location along the fluid path between the syringe and the vial so as to remove unwanted particulates from the reconstituted solution.

Finally, after the solution has been reconstituted in the above manner, it is then ready for subsequent injection into the patient by any of a variety of means commonly used for such reconstituted medicaments. For example, if one uses a syringe which does not have an exposed metal cannula, a suitable needle or other means by which the reconstituted fluid can be injected into the patient will need to be attached to the syringe. As would be recognized by one of ordinary skill in this art, there are many conventional means that would be available to effect the injection of the reconstituted fluid into the patient, including simply screwing or otherwise attaching a suitable needle by which the user can inject the reconstituted medicament into his or her bloodstream. One particular type of needle that will be useful in effecting injection of the reconstituted solution will be one known as a "butterfly" needle which consists of a steel cannula preferably about 2 to 3 inches long to which is attached a pair of plastic "butterfly" wings and tubing which has an end with a female luer fitting to allow attachment to the end of the syringe. In this "butterfly" needle, the flexible plastic wings allow for easy handling of the needle so that the patient can inject it safely and conveniently, and additionally tape the butterfly wings to the skin if necessary to create a one-hand infusion means.

Similarly, the patient may also have a previously implanted port which pierces through the skin, and thus once the fluid is reconstituted in the syringe, it may be injected directly into the implanted port which avoids the need for the patient to search for a suitable vein when injection is desired. This mode is particularly preferred in situations where the patient is a child. Finally, still other modes of injection can be employed as needed, such as by using the syringe to load an IV bag or other suitable sterile container which is designed to allow controlled administration of the reconstituted product into the patient.

In short, the reconstitution device of the present invention can be constructed and employed in a variety of ways which will be useful and advantageous in the administration of a lyophilized or powdered medicament which must be reconstituted before use, and thus one of ordinary skill in this art would recognize a variety of embodiments which fall within the scope of the present invention, as set forth in the claims appended hereto.

What is claimed is:

1. A reconstitution device for use in reconstituting a powdered medicament contained in a sterilized sealed vial prior to injection into a patient comprising:

(a) a housing having an upper section with an opening in its upper end capable of receiving a syringe, a lower section with an opening capable of receiving and housing a vial and maintaining the vial in roughly co-axial alignment with a syringe housed in said upper section;

(b) a middle section connecting said upper and lower sections of said housing having a central aperture which provides a passageway for the transfer of fluid between said upper and lower sections of said housing; and (c) a hollow elongated slotted spike extending downwardly from said central aperture for a length sufficient to ensure that the lower end of the spike will pierce the top of a sealed vial when said vial is housed in the lower section of said housing, said slot extending from a point at the lower end of the spike to a point near the base of the spike so as to allow (i) rapid pressure equalization in the vial when the spike pierces the seal of the vial; and (ii) drainage of reconstituted medicament when the device is inverted so as to dispense the reconstituted medicament from the vial into the syringe.

2. A reconstitution device according to claim 1 wherein the interior surface of said upper section is roughly cylindrical.

3. A reconstitution device according to claim 1 further comprising ribs on the interior surface of said upper section.

4. A reconstitution device according to claim 1 wherein the lower end of said lower section is flanged.

5. A reconstitution device according to claim 1 further comprising a means to retain a syringe in the upper section of said housing.

6. A reconstitution device according to claim 5 wherein said means to retain a syringe in the upper section of said housing comprises a luer fitting.

7. A reconstitution device according to claim 1 further comprising a filter disposed along the passageway of fluid between the vial and the syringe.

8. A reconstitution device according to claim 7 wherein the pore size of said filter is in the range of from about 80 microns to about 160 microns.

9. A reconstitution device according to claim 7 wherein the filter is comprised of a material selected from the group consisting of nylon and polyester.

10. A reconstitution device according to claim 1 which is comprised of a sterilizable plastic material.

11. A reconstitution device according to claim 10 wherein the device is comprised of a material selected from the group consisting of polycarbonates, acrylics and acrylic butyl styrene.

12. A reconstitution device according to claim 1 which is comprised of a transparent plastic material.

13. A reconstitution device according to claim 1 which is comprised of an opaque plastic material.

14. A reconstitution device according to claim 1 wherein the lower section has openings to allow visual assessment of the positioning of the hollow vented spike.

15. A reconstitution device according to claim 1 wherein the lower section of said housing is of a length so that the bottom end of said lower section does not extend to the bottom of a vial which is housed in the lower section.

16. A reconstitution device according to claim 1 further comprising a tip protector which is positioned over the hollow vented spike prior to use.

17. A reconstitution device according to claim 1 wherein the lower end of said lower section is flared so that the exterior opening of the lower section is larger in diameter than the inner end of said lower section.

18. A reconstitution device according to claim 1 wherein the lower section is of a size which will receive a vial having a volume in the range of from about 10 ml to about 50 ml.

19. A reconstitution device according to claim 1 wherein the lower section will receive a vial having a volume of about 30 ml.

20. A reconstitution device according to claim 1 in combination with a syringe housed in said upper section of said housing.

21. A reconstitution device according to claim 20 in which the syringe comprises a glass barrel encased in a plastic sheath.

22. A reconstitution device according to claim 20 further comprising a cannula having a blunt end which faces the reconstitution device and a sharp end which faces the interior of the syringe, and a stoppered compartment containing a sterile fluid which is pierced by the sharp end of the cannula prior to use.

23. A reconstitution device according to claim 20 which is sterilized prior to use.

24. A reconstitution device according to claim 20 further comprising a tip protector covering the hollow vented spike of the lower section of said housing.

25. A reconstitution device according to claim 20 further comprising tamper-evident packaging which alerts the user if the syringe has previously been separated from the reconstitution device.

26. A reconstitution device according to claim 1 in combination with a vial housed in said lower section of said housing.

27. A reconstitution device according to claim 1 in combination with a syringe housed in said upper section of said housing and a vial housed in said lower section of said housing.

28. A method of reconstituting a medicament contained in a sterilized sealed vial comprising the steps of:

(a) providing a syringe containing a sterile fluid capable of reconstituting a medicament;

(b) providing a reconstitution device according to claim 1;

(c) positioning the syringe in the upper section of said reconstitution device and positioning the sealed vial containing the medicament in the lower section of said reconstitution device so that the hollow slotted spike of the device pierces the seal on the vial and enters the interior of the vial;

(d) expelling the fluid in the syringe through the hollow slotted spike and into the vial so as to reconstitute the medicament in the vial.

29. A method according to claim 28 further comprising the step of withdrawing the reconstituted fluid from the vial back into the syringe.

30. A method according to claim 28 wherein the medicament is a lyophilized or powdered medicament.

31. A method according to claim 28 wherein the medicament comprises a blood factor concentrate.

32. A method according to claim 28 wherein the medicament comprises factor VIII.

33. A method according to claim 28 wherein the sterile fluid comprises a fluid selected from the group consisting of sterile water, saline solution, half-normal saline, dextrose and other diluents.

* * * * *